(12) United States Patent  (10) Patent No.: US 7,250,050 B2
Ryan  (45) Date of Patent: Jul. 31, 2007

(54) TUBAL STERILIZATION DEVICE HAVING SESQUIPOLAR ELECTRODES AND METHOD FOR PERFORMING STERILIZATION USING THE SAME

(75) Inventor: Thomas P. Ryan, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 432 days.

(21) Appl. No.: 10/862,210

(22) Filed: Jun. 7, 2004

(65) Prior Publication Data

US 2005/0273094 A1    Dec. 8, 2005

(51) Int. Cl.
    *A61B 18/18*   (2006.01)
(52) U.S. Cl. ........................................... 606/50
(58) Field of Classification Search .............. 606/41, 606/32, 46, 48–50
    See application file for complete search history.

(56) References Cited

U.S. PATENT DOCUMENTS

| | | | |
|---|---|---|---|
| 4,823,791 A | 4/1989 | D'Amelio et al. | |
| 5,098,431 A | 3/1992 | Rydell | |
| 5,122,137 A | 6/1992 | Lennox | |
| 5,383,876 A * | 1/1995 | Nardella | 606/49 |
| 5,403,311 A * | 4/1995 | Abele et al. | 606/49 |
| 5,507,743 A * | 4/1996 | Edwards et al. | 606/41 |
| 5,556,396 A | 9/1996 | Cohen et al. | |
| 6,001,095 A | 12/1999 | de la Rama et al. | |
| 6,066,139 A | 5/2000 | Ryan et al. | |
| 6,077,261 A | 6/2000 | Behl et al. | |
| 6,346,102 B1 | 2/2002 | Harrington et al. | |
| 6,352,549 B1 | 3/2002 | Everett | |
| 6,378,524 B1 | 4/2002 | Jones | |
| 6,432,116 B1 | 8/2002 | Callister et al. | |
| 6,485,466 B2 | 11/2002 | Hamilton | |
| 6,488,678 B2 | 12/2002 | Sherman | |
| 6,706,039 B2 * | 3/2004 | Mulier et al. | 606/41 |
| 6,837,888 B2 * | 1/2005 | Ciarrocca et al. | 606/41 |
| 2002/0020417 A1 | 2/2002 | Nikolchev et al. | |
| 2002/0100480 A1 | 8/2002 | Nikolchev et al. | |
| 2002/0148476 A1 | 10/2002 | Farley et al. | |
| 2005/0043728 A1 * | 2/2005 | Ciarrocca | 606/48 |

* cited by examiner

*Primary Examiner*—Michael Peffley
*Assistant Examiner*—Pete Vrettakos

(57) ABSTRACT

A tubal sterilization device having sesquipolar electrodes includes a hollow catheter defining an interior passageway, the catheter including a first end for insertion transcervically into a patient, and a second end opposite the first end for grasping and manipulation by a physician. The device further includes an electrode tip situated at the first end of the catheter. The electrode tip includes a first portion having a first electrode, the first portion being preferably formed generally conically in shape so that it may be snugly fit into the tubal osteum of the fallopian tube. The electrode tip further includes a second portion having a second electrode which is a coil formed from a wire which is helically wrapped about an insulating spacer or support. The second portion of the electrode tip with the second electrode may be retracted within a bore formed axially within the first portion of the electrode tip and may selectively extended therefrom for placement within the intramural segment of the fallopian tube. A slider linkage within the hollow catheter moves the second portion and second electrode between its retracted position and extended position. Bipolar RF (radio frequency) energy is provided to the first and second electrodes to cause the selective heating of tissue within the intramural segment of the fallopian tube.

8 Claims, 7 Drawing Sheets

TUBAL STERILIZATION DEVICE HAVING SESQUIPOLAR ELECTRODES AND METHOD FOR PERFORMING STERILIZATION USING THE SAME

BACKGROUND OF THE INVENTION

1. Field of the Invention

The present invention generally relates to devices for occluding a body lumen, and more specifically relates to a permanent contraceptive or sterilization device for occluding a reproductive tract or lumen. Even more particularly, the present invention relates to a device which causes sterility in women by occluding the female reproductive fallopian tubes using RF (radio frequency) energy.

2. Description of the Prior Art

Many methods of female sterilization have been investigated. One method is surgical tubal ligation, which is a procedure in which the uterine tubules are tied and cut or clamped through an incision made through the wall of the abdomen. Tubal ligation done with a laparotomy requires a surgical incision in the abdomen under general anesthesia. Drawbacks of this procedure necessarily include the risks inherent with anesthesia and the permanent scar formation at the site of the incision. Another technique involves transcervically instilling the sclerosing agent quinacrine into the uterus and fallopian tubes to create a permanent closure of the fallopian tubes. Drawbacks of this procedure include the need of repeat applications and a significant level of side effects.

A further procedure involves transcervically injecting a curable elastomeric composition such as silicone into the fallopian tubes in an amount sufficient to fill the portion of the fallopian tube adjacent the uterus, which composition is allowed to cure and solidify to non-surgically block the tube. This technique is time consuming and requires a high level of technical skill and had poor results with sterilization.

There are also permanent contraceptive or sterilization devices which are transcervically delivered and mechanically anchored within the fallopian tubes and which promote tissue ingrowth into the device and scar tissue formation which eventually may totally occlude each fallopian tube. Such a device is disclosed in U.S. Pat. No. 6,432,116 (Callister et al.) and published U.S. patent application Ser. No. 09/912,067 (Nikolchev et al.).

Sterilization has also been performed using RF (radio frequency) energy. As disclosed in U.S. Pat. No. 5,556,396 (Cohen et al.), an electrically energizable electrode is advanced into the fallopian tube and energized to thermally damage the fallopian tube, thereby causing enough scarring of the fallopian tube to permanent occlude it. Further sterilization devices using RF energy are disclosed in U.S. Pat. No. 6,066,139 (Ryan et al.) and U.S. Pat. No. 6,346,102 (Harrington et al.).

OBJECTS AND SUMMARY OF THE INVENTION

It is an object of the present invention to provide a transcervically deliverable tubal sterilization device which obviates the need for surgery.

It is another object of the present invention to provide a sterilization device which is flexible to facilitate placement in the fallopian tube transcervically, which placement may be guided visually using a hysteroscope.

It is still another object of the present invention to provide a tubal sterilization device which uses commonly accepted RF (radio frequency) energy.

It is a further object of the present invention to provide a tubal sterilization device employing a catheter which only enters the fallopian tube in the wall of the uterus, thus reducing the risk of perforation.

It is yet a further object of the present invention to provide a tubal sterilization device which effectively causes occlusion of the fallopian tube by heating the intramural portion of the tube, thereby being safer and reducing any risk of heating adjacent structures or organs, such as the bladder or bowel.

It is still another object of the present invention to provide a sterilization device for sterilizing human females, which device employs bipolar RF energy to avoid stray currents and unnecessary heating outside of the intended target zone.

It is yet a further object of the present invention to provide a tubal sterilization device which applies RF energy to heat the fallopian tubal wall and which monitors the temperature of the tissue to ensure a reproducible and safe heating of the tissue.

It is a further object of the present invention to provide a tubal sterilization device in which no foreign object remains in the body after the sterilization procedure, which might otherwise cause a reaction or affect imaging of the patient or migrate within the patient.

It is yet another object of the present invention to provide a tubal sterilization device which causes occlusion of the fallopian tube by natural healing rather than by foreign body placement, which foreign body may be displaced by peristalsis.

It is still another object of the present invention to provide a method for performing sterilization using a sterilization device formed in accordance with the present invention.

It is yet another object of the present invention to provide a tubal sterilization device which is shaped to help blindly position the device into the tubal osteum.

It is a further object of the present invention to provide a tubal sterilization device which is shaped to help open the tubal osteum without the need to insufflate the uterus with carbon dioxide gas or saline solution.

It is yet a further object of the present invention to provide a tubal sterilization device which may be remotely reconfigured by a physician to make the device easier to insert in a desired location within the fallopian tube of a patient.

In accordance with one form of the present invention, a sterilization device which causes occlusion to the fallopian tube of a patient is designed to be transcervically positioned in the intramural segment of the tubal osteum without perforating the tube. Preferably, the tubal sterilization device includes a hollow catheter defining an interior passageway, the catheter including a first end for insertion transcervically into a patient, and a second end opposite the first end for grasping and manipulation by a physician. The device further includes an electrode tip situated at the first end of the catheter. The electrode tip includes a first portion having a first electrode situated thereon, and a second portion having a second electrode situated thereon. The first portion of the electrode tip is preferably generally conically shaped so that it will closely contact and be seated in the tubal osteum at the entrance of the fallopian tube when the catheter is transcervically inserted into the patient. The second end of the electrode tip is preferably formed as a helical coil of wire wound around an insulating support. The second portion of the electrode tip, bearing the helically wound electrode, may be selectively retracted within a bore formed axially through the conically-shaped first portion, when the first end of the catheter is being properly positioned at the tubal osteum, and extended therefrom so that the helically wound second electrode is spaced apart from the first electrode to extend into the intramural segment of the fallopian tube.

A slider linkage extends through the catheter passageway and is coupled to the movable second portion of the electrode tip. The slider linkage is axially movable within the catheter passageway so that the physician, when he or she pulls or pushes on the slider linkage or a handle connected thereto, retracts or extends, respectively, the second portion of the electrode tip having the helically wound wire.

The helically wound wire electrode is the "active" electrode and is primarily where heating of the surrounding tissue of the fallopian tube occurs. The electrode on the conically-shaped first portion of the electrode tip is the "return" electrode. The surface area of the first electrode is preferably significantly greater than the surface area of the helically wound, first electrode so that relatively little heating of the tissue surrounding the first electrode occurs.

When the second electrode is extended from the first electrode and properly positioned within the intramural segment of the fallopian tube, the physician energizes both electrodes. Bipolar RF (radio frequency) energy is provided to the two electrodes by an RF generator. The temperature of the surrounding tissue heated preferably in the vicinity of the second electrode (i.e., the helically wrapped wire) is monitored by a temperature sensor, such as a thermocouple or the like, to prevent overheating or charring of the surrounding tissue of the fallopian tube. The temperature sensor provides a signal indicative of the temperature of the surrounding tissue to a control circuit, which may include a microprocessor, and which effectively monitors the temperature and compares it to a range of desired temperatures. In response to this comparison, the control circuit provides a control signal to the RF generator to control the power of the RF energy provided by the generator to the electrodes.

These and other objects, features and advantages of the present invention will be apparent from the following detailed description of illustrative embodiments thereof, which is to be read in connection with the accompanying drawings.

DETAILED DESCRIPTION OF THE PREFERRED EMBODIMENTS

Figure 1:
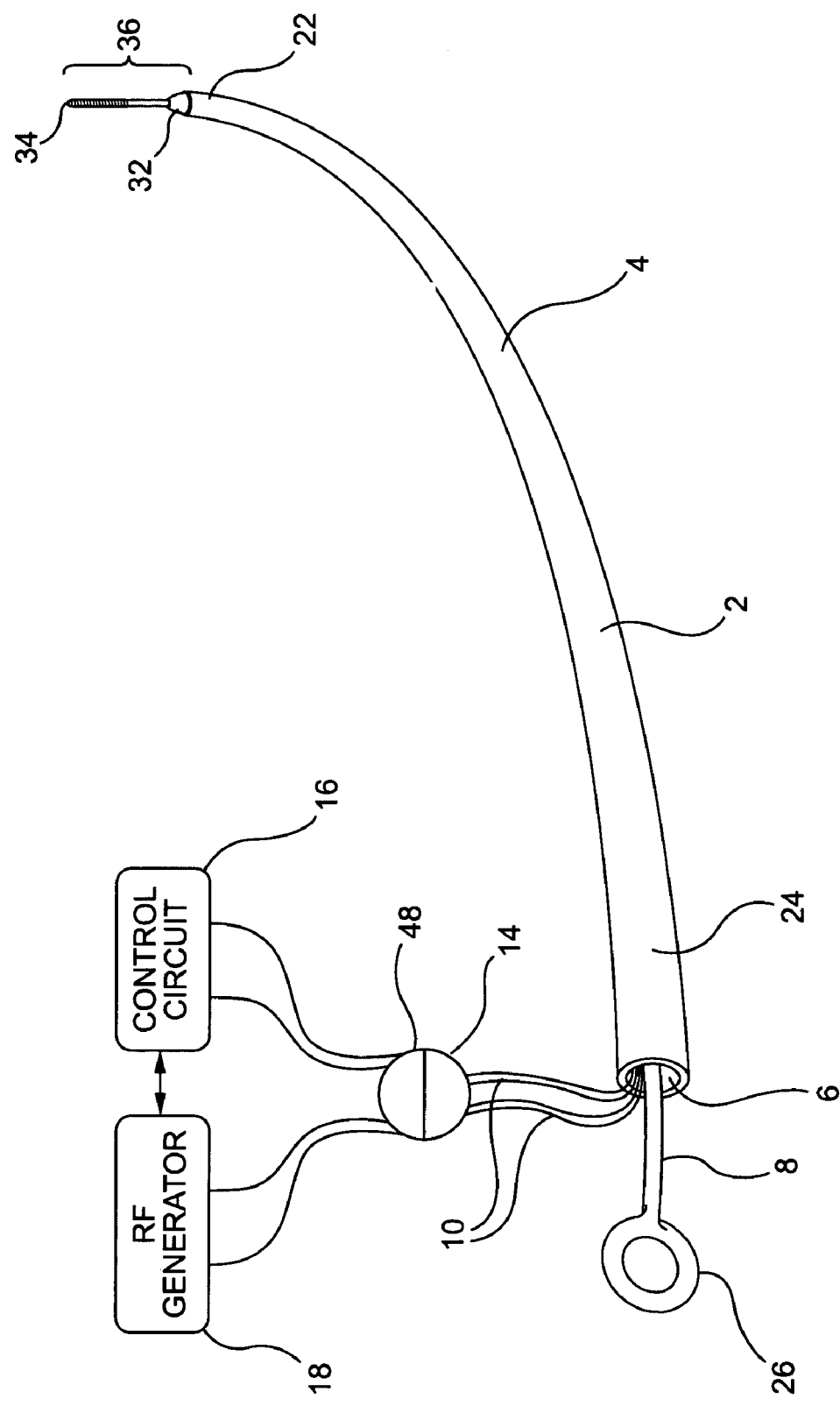
FIG. 1 is an isometric view of a tubal sterilization device having sesquipolar electrodes formed in accordance with one form of the present invention.
Figure 2:
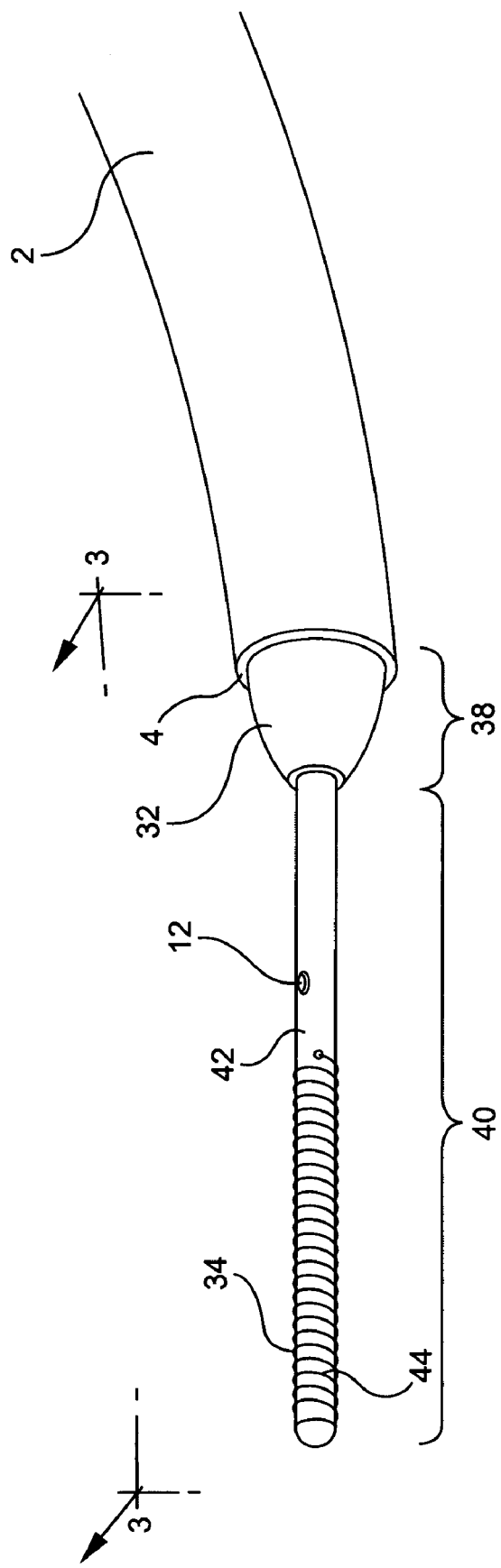
FIG. 2 is an isometric view of the electrode tip portion of the tubal sterilization device of the present invention, where the electrode tip portion is shown in an extended state.
Figure 3:
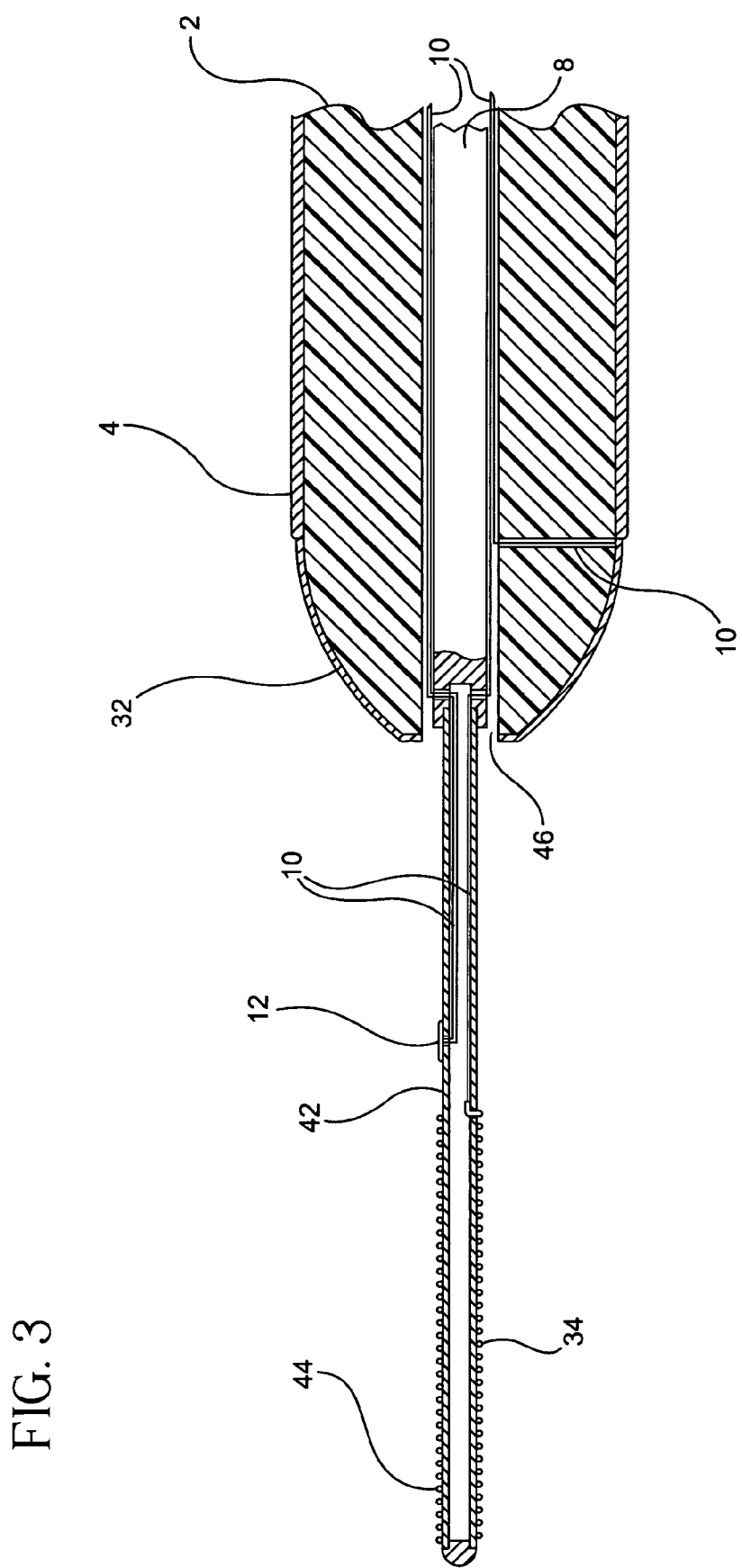
FIG. 3 is a cross-sectional view of the electrode tip portion shown in FIG. 2, taken along line 3-3 of FIG. 2.
Figure 4:
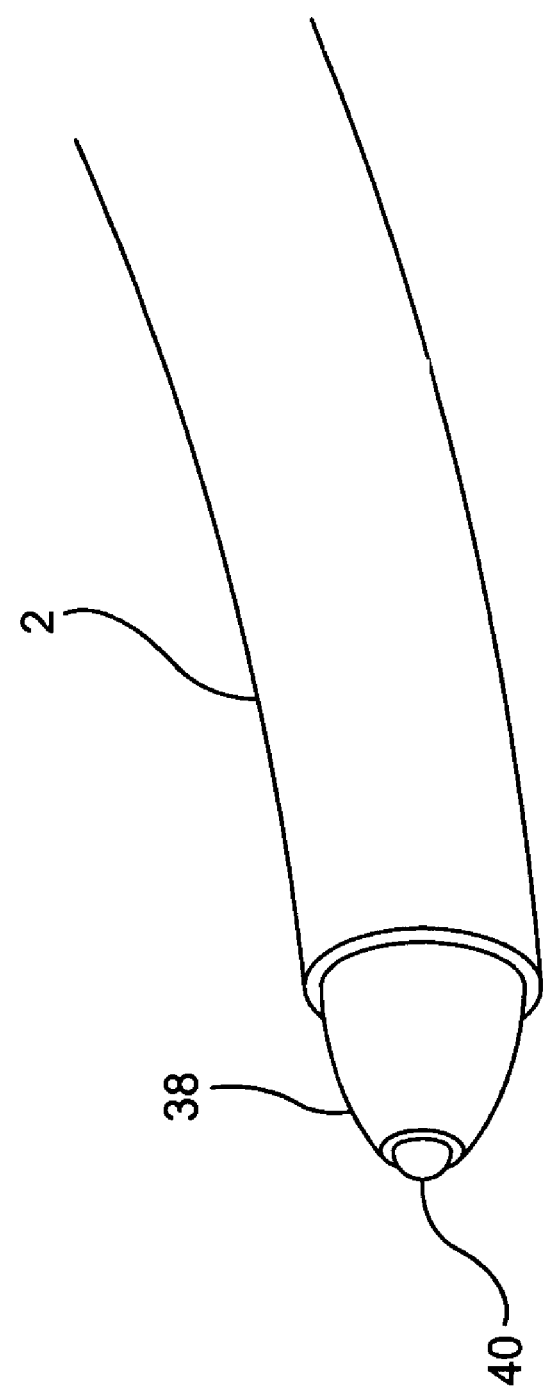
FIG. 4 is an isometric view of the electrode tip portion of the tubal sterilization device of the present invention, where the electrode tip portion is shown in a retracted state.
Figure 5:
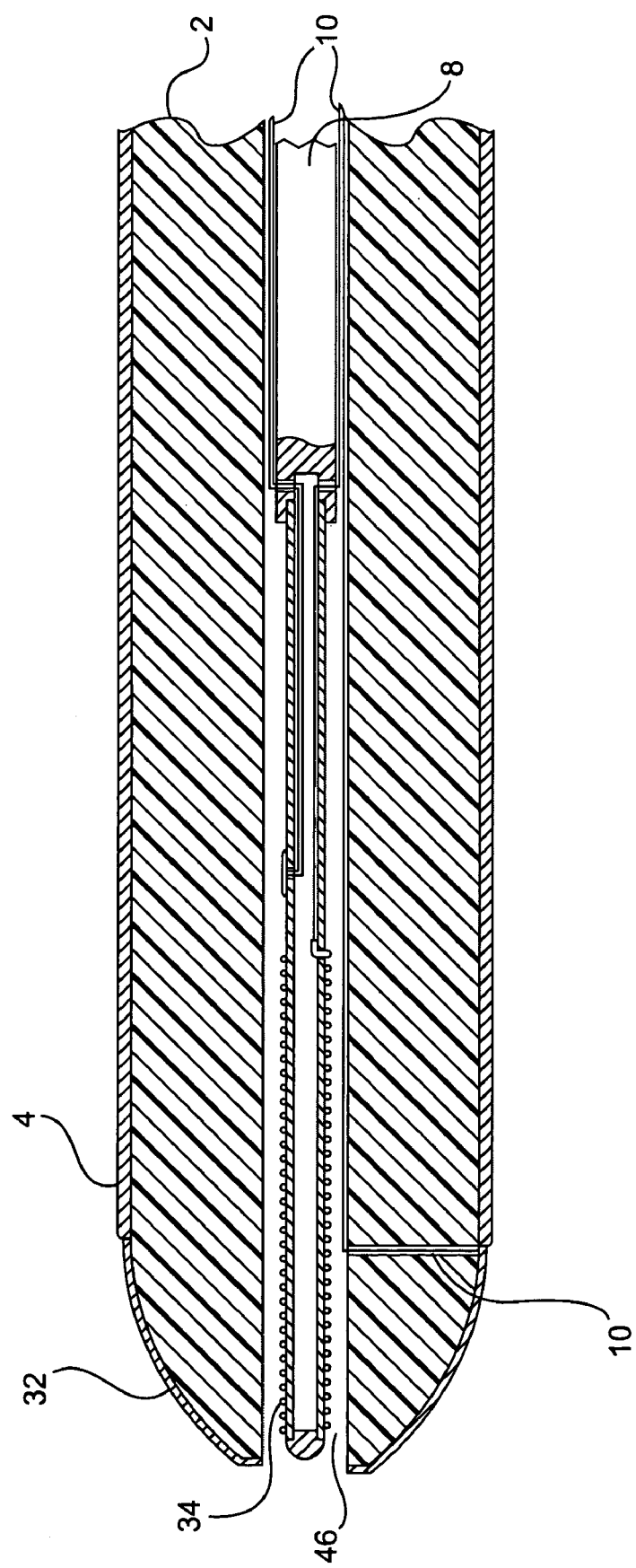
FIG. 5 is a cross-sectional view of the electrode tip portion shown in FIG. 4, taken along line 5-5 of FIG. 4.

Turning initially to FIG. 1 of the drawings, a tubal sterilization device having sesquipolar electrodes is generally shown. The sterilization device basically includes a hollow catheter 2 which is an elongate member having an outer housing or cover 4 and which defines an interior passageway 6. As will be described in greater detail, the interior passageway 6 allows a slider linkage 8 in the form of a cable, flexible push rod or wire to pass therethrough, as well as wires 10 or other electrical connections which are connected to the electrodes and, as will be described in greater detail, a temperature sensor 12 at one end of the catheter 2 and which are further connected to an electrical connector 14 at the other end of the catheter for connection to a control circuit 16 and an RF (radio frequency) signal generator 18.

More specifically, the catheter 2, or at least a portion thereof, is generally circular in cross-section and is particularly sized for transcervical insertion into a fallopian tube 20 of a patient. The catheter has a first end 22, which may also be referred to as the patient end, which is inserted transcervically into the patient, and a second end 24 opposite the first end for grasping and manipulation by a physician. The second end 24 may include a handle 26 or the like (shown generally as a ring) to facilitate handling by the physician. It is the first end 22 of the catheter 2 which is of primary interest in the present invention, as this is where the electrodes are located, as will be described in greater detail.

Figure 6:
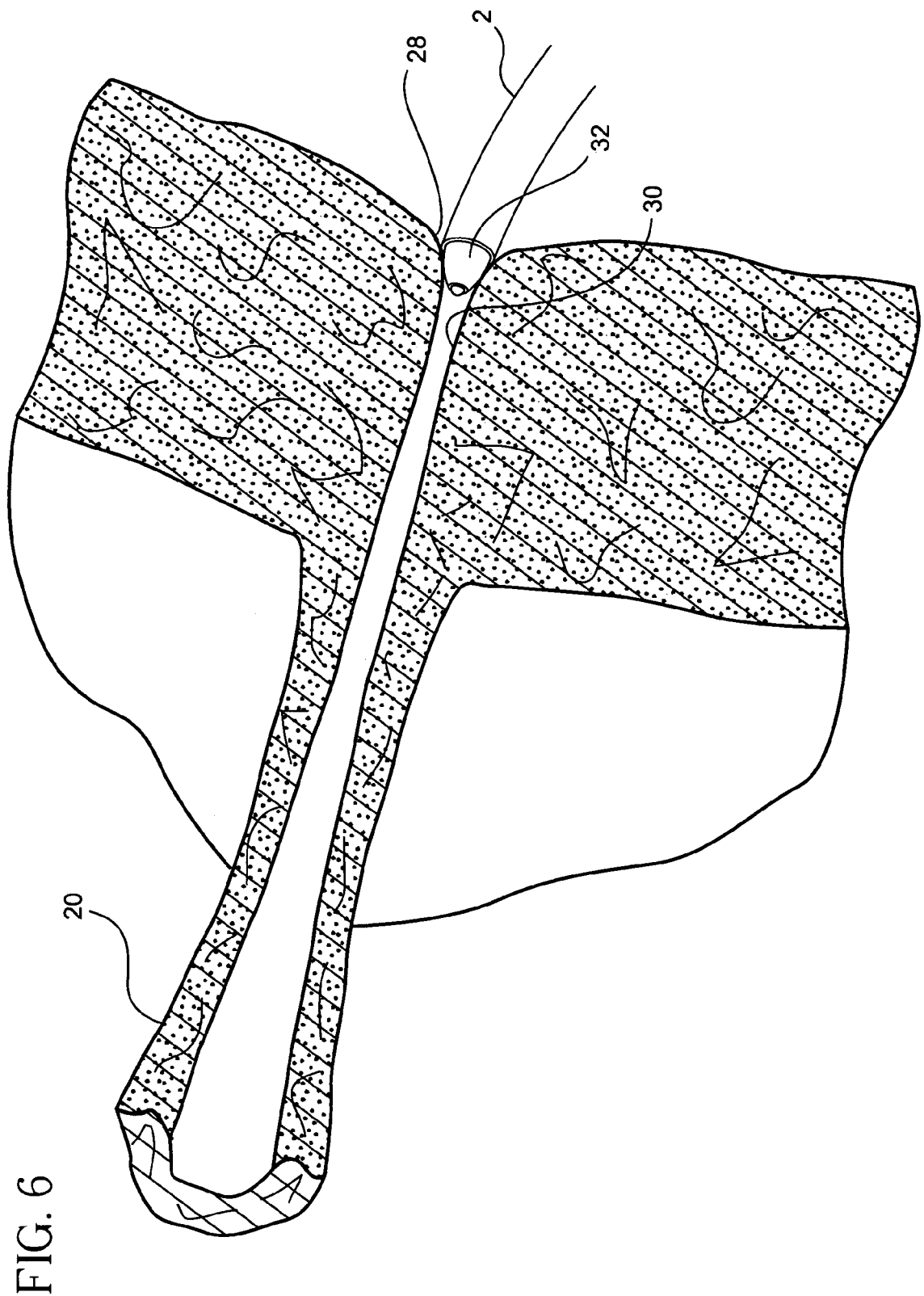
FIG. 6 is diagrammatic, cross-sectional view of specific body portions of a patient and the tubal sterilization device of the present invention, illustrating the proper placement of the device within the patient.
Figure 7:
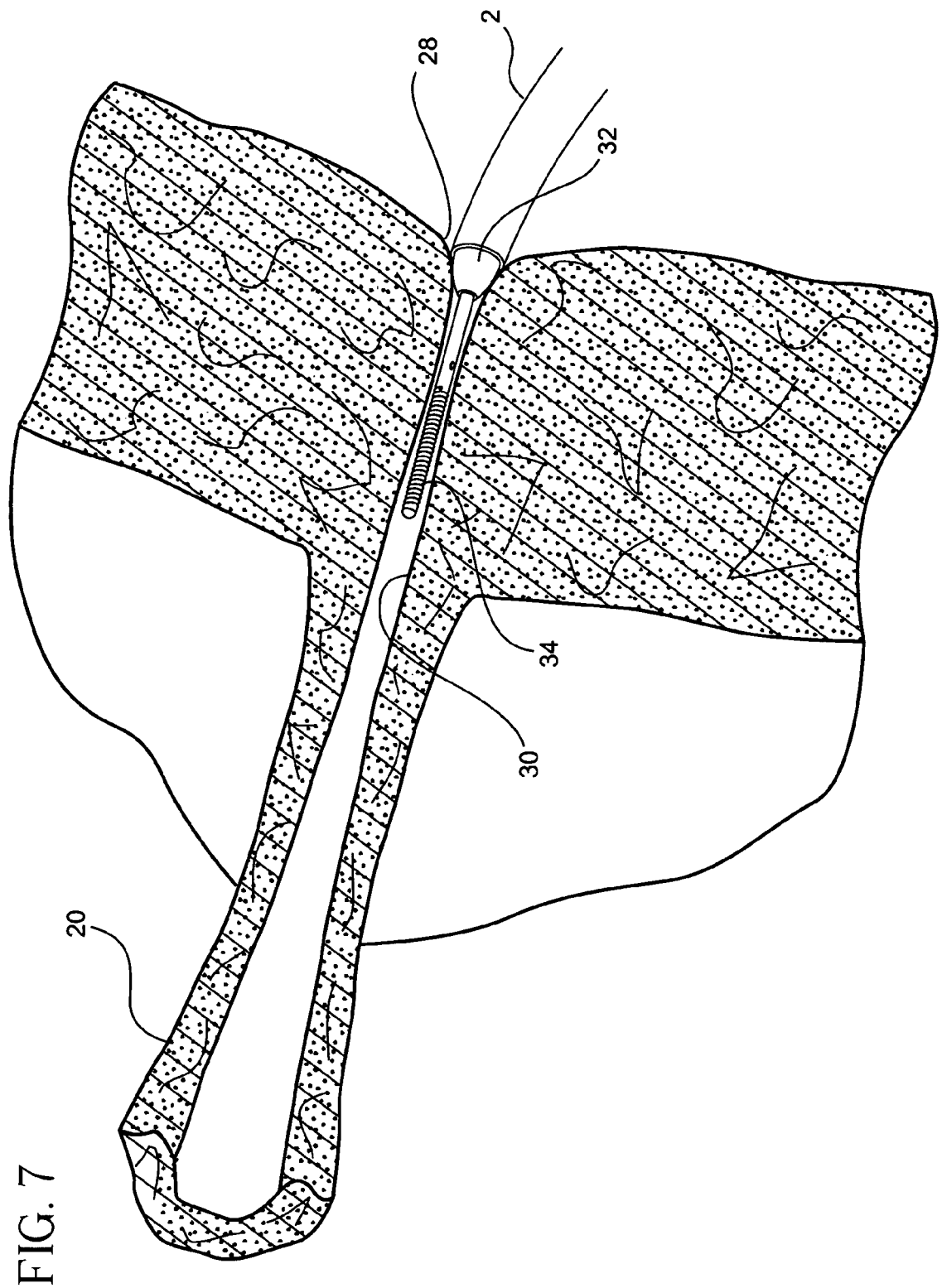
FIG. 7 is a diagrammatic, cross-sectional view of specific body portions of a patient and the tubal sterilization device of the present invention, as illustrated by FIG. 6, showing the electrode tip of the tubal sterilization device in the extended position.

Preferably, the first end 22 of the hollow catheter 2 is directed by the physician by his manipulation of the second end 24 so that it is placed through the cervix of the patient and into the uterine cavity and, from there, it is moved to the tubal osteum 28, which is the entrance to the fallopian tube 20 (see FIGS. 6 and 7). There is a thick muscular wall in this initial portion of the tube called the intramural segment 30. As will be described in greater detail, a portion of the first end 22 of the catheter having one electrode 32 is placed snugly against the tubal osteum 28, while another portion of the first end 22 of the catheter having a second electrode 34 is inserted into the intramural segment 30 of the fallopian tube 20. It is here, in the intramural segment 30 of the fallopian tube, where heating by the second electrode 34 takes place. Use of the tubal sterilization device of the present invention will be safer and reduce any risk of heating adjacent structures such as the bladder or bowel if the sterilization device is properly positioned as described above. Placement and positioning of the catheter tip of the tubal sterilization device may be directly visualized with a hysteroscope.

The first end 22, or patient end, of the catheter 2 has an electrode tip 36 situated thereat. The preferred form of the electrode tip 36 is shown in FIGS. 2-5. More specifically, the electrode tip 36 includes a first portion 38 having a first electrode 32 situated thereon, and a second portion 40 having a second electrode 34 situated thereon. The first portion 38 and the second portion 40 of the electrode tip 36, and their corresponding electrodes 32, 34, are selectively spaced from one another. Preferably, the first portion 38 of the electrode tip, with its first electrode 32, is fixedly mounted to the end of the catheter 2. The second portion 40 of the electrode tip, with the second electrode 34, however, is preferably movable axially relative to the first portion 38 and its first electrode 32.

As mentioned previously, and as illustrated in FIG. 1 of the drawing, a slider linkage 8, in the form of a flexible cable, rod, wire or the like, extends through the catheter passageway 6 and is coupled to the second portion 40 of the electrode tip 36. The slider linkage 8 is axially movable within the catheter passageway 6 and may be pushed inwardly and pulled outwardly through the catheter 2 by the physician manipulating a handle 26, loop, or the like attached to the slider linkage 8 at the second end 24 of the catheter. Axial movement of the slider linkage 8 thus causes corresponding axial movement of the second portion 40 of the electrode tip 36, and its second electrode 34, with respect to the first portion 38 of the electrode tip and its first electrode 32.

The first portion 38 of the electrode tip is preferably formed as being generally conical in shape. The purpose for this particular shape is so that it may abut against and snugly fit into the tubal osteum 28. This shape facilitates the physician's manipulation and positioning of the electrode tip portion 36 of the catheter 2 in the desired position at the entrance of the fallopian tube 20. Furthermore, the conical shape provides a blunt tip for the transcervical insertion of the catheter into the patient so as not to perforate any delicate tissue during proper positioning of the catheter first end 22. Preferably, the conically-shaped first portion 38, with its first electrode 32, has a diameter of between about 5 millimeters and about 10 millimeters. The conical surface of the first portion 38 of the electrode tip 36 includes an electrically conductive coating or material, such as silver, gold or the like, which forms the first electrode 32.

The movable second portion 40 of the electrode tip 36 preferably includes an axially elongated, insulated spacer 42 or support, on the outer surface of which is helically wrapped an uninsulated and electrically conductive wire in the form of a coil 44. The coil 44 preferably defines the second electrode 34. Alternatively, the second electrode 34 may be a solid metal cylinder supported or attached to the insulated spacer, or like the first electrode 32, a material or conductive coating (silver, gold or the like) which is deposited on the insulated spacer such as by vapor deposition or other suitable methods to make the second electrode 34. Preferably, the second electrode 34 is sized to be between about 0.5 millimeters and about 1.0 millimeters in diameter and between about 5 millimeters and about 10 millimeters in length. The second portion 40 of the electrode tip 36 may be rigid, such as where the second electrode 34 is formed from stainless steel or the like, or may be flexible, such as where the second electrode 34 is made from a coil 44 of 30 gauge silver coated wire. The second portion 40 of the electrode tip, with its second electrode 34, may be axially straight or have a natural bend or curvature.

As mentioned previously, the second portion 40 of the electrode tip, with the second electrode 34, may extend from or be retracted into the conically-shaped first portion 38 of the electrode tip 36 when the physician causes the slider linkage 8 to move axially forward and backward in the catheter passageway 6. The retraction and extension of the second portion 40 of the electrode tip 36 with respect to the first portion 38 are shown in FIGS. 2-5.

More specifically, the conically-shaped first portion 38 of the electrode tip 36 includes a bore 46 formed axially therethrough, which bore 46 communicates with the passageway 6 of the catheter 2. The bore 46 is dimensioned to allow the insulated spacer 42 or support of the second portion 40 of the electrode tip 36, and the coiled second electrode 34 wound thereon, to be selectively received thereby. Accordingly, when the patient end 22 of the catheter 2 is being transcervically inserted into the patient by the physician, the second portion 40 of the electrode tip 36, with the second electrode 34, may reside in a retracted state within the bore 46 of the first portion 38 of the electrode tip 36 so that it does not extend out beyond the confines of the conically-shaped first portion 38 and so that it cannot perforate any sensitive tissue during its insertion and positioning at the tubal osteum 28 of the fallopian tube 20.

Once the first tip portion 38 is in proper position at the tubal osteum 28, as shown in FIG. 6, the slider linkage 8 is moved by the physician so that the second portion 40 of the electrode tip 36, with the second electrode 34, is axially moved from its retracted position within the bore 46 of the first portion 38 to an extended position such that the second electrode 34 is spaced apart a desired distance from the first electrode 32 and the first portion 38 of the electrode tip 36. The separation distance between the distal end of the first electrode 32 and the proximal end of the second electrode 34 is preferably between about 5 millimeters and 20 millimeters. The second electrode 34 will then be extended sufficiently into the intramural segment 30 of the fallopian tube 20 and it is here that heating of the surrounding tissue and the formation of a lesion take place, as shown by FIG. 7.

Once the second electrode 34 has been extended a desired distance from the first electrode 32, the physician energizes the two electrodes by applying preferably bipolar RF (radio frequency) energy to them. A wire 10, flexible conductive run or other connection is attached to the first electrode 32 and passes either through the passageway 6 of the catheter 2 or under the outer covering or housing 4 of the catheter to an external connector 14 at the catheter second end 24. Similarly, the second electrode 34 is connected by a wire 10, flexible conductive run or other connection through the passageway 6 or under the outer covering 4 of the catheter 2 to the connector 14. Preferably, the second electrode 34 may be an exposed portion of the inner conductor of an insulated wire and the insulated spacer 42 or support may be the outer insulation of the wire, where the exposed inner conductor is helically wrapped about the outer insulation of the wire. In this form, the second electrode 34 is connected through the inner conductor of the wire, which wire may be either connected to the slider linkage 8 or, even more preferably, may form part or all of the slider linkage which is axially moved within the catheter passageway 6 by the physician. The inner conductor of the wire may also be connected to the external connector 14.

A mating connector 48 couples to the first and second electrode wire connector 14, and the mating connector 48 is wired to an RF energy signal generator 18 which provides an RF bipolar voltage to the first and second electrodes 32, 34 through the connectors 14, 48 and interconnecting wires 10.

The first and second electrodes 32, 34 are responsive to RF (radio frequency) energy provided by the RF signal generator 18. The electrodes 32, 34 are activated with about 5 watts of RF energy, each electrode being separated from the other so that each electrode may be oppositely polarized to allow the application of bipolar energy. Preferably, only sufficient energy is applied to the electrodes 32, 34 to result in tissue temperatures between about 95° Celsius and about 105° Celsius.

Even more preferably, the tubal sterilization device of the present invention may include a temperature sensor 12, such as a thermistor, thermocouple, thermopile, fiber optic sensor, resistance temperature device (RTD) or the like, to measure the temperature of the surrounding tissue undergoing heating. The temperature sensor 12 is preferably mounted on the electrode tip 36 and, even more preferably, on the second portion 40 having the second electrode 34 of the electrode tip. It is preferred that the second electrode 34 provides most, if not all, of the heating to the surrounding tissue it contacts, and very little heating is caused by the first electrode 32, as will be further described. Accordingly, the preferred location for the temperature sensor 12 is on the second portion 40 of the electrode tip.

The temperature sensor 12 may be mounted on the second portion 40 of the electrode tip 36 and insulated from the second electrode 34, and connected by wires 10, flexible conductive runs or other connections which may pass through the interior of the insulated spacer 42 or support for the second electrode 34 and either through the catheter passageway 6 or under the outer covering or housing 4 of the catheter 2 to the external connector 14 situated at the second end 24 of the catheter. The mating connector 48 connects the temperature sensor wires 10 to the control circuit 16. As mentioned previously, the temperature sensor 12 measures the temperature of the tissue which is heated by at least the second electrode 34, and generates an electrical signal indicative of that temperature, which electrical signal is provided to and processed by the control circuit 16. The control circuit 16 thus monitors the heat of the surrounding tissue and compares it to a desired temperature range, which is preferably between about 95° Celsius and about 105° Celsius, and generates a control signal to the RF signal generator 18 based on this comparison to adjust the power of the RF energy applied by the generator to the electrodes 32, 34 in a continual feedback arrangement. The control circuit 16 may include a microprocessor or other circuitry to perform this control function. Thus, the temperature sensor 12, control circuit 16, RF energy signal generator 18 and the electrodes 32, 34 define together a feedback loop so that only a controllable level of RF power is provided to the electrodes to prevent charring or overheating of the targeted area.

For a more detailed explanation of a temperature sensor, an RF generator and a control circuit, for example, a microprocessor, reference is made to U.S. Pat. No. 6,066,139 (Ryan et al.), the disclosure of which is incorporated herein by reference.

When the electrode tip 36 is properly positioned with the first portion 38 and first electrode 32 being received by the tubal osteum 28 and the second portion 40 and second electrode 34 being received by the intramural segment 30 of the fallopian tube 20, the electrodes are energized with about 5 watts of RF energy. Power is adjusted to control the temperature and further to avoid steam formation and the resulting pressure waves. RF energy is applied for a duration of preferably between about 0.5 minutes and about 5 minutes at a power setting of about 5 watts, and more preferably between about 1 minute and about 2 minutes at a power setting of about 5 watts.

After heat has been applied to the targeted area of the fallopian tube 20, the electrodes 32, 34 are deenergized, and the second portion 40 of the electrode tip, with its second electrode 34, is then retracted into the bore 46 of the first portion 38 of the electrode tip so that the second electrode 34 does not extend outside the confines of the first portion 38 of the electrode tip and so as not to injure or perforate any tissue as the catheter is being withdrawn by the physician from the fallopian tube, uterine cavity and cervix.

As mentioned previously, it is desired if the heating occurs in the intramural segment 30 of the fallopian tube 20 at or about the second electrode 34. This electrode may be referred to as the "active" electrode, whereas the first electrode 32 may be referred to as the "return" electrode. To ensure that heating substantially takes place only at the second electrode 34, which is positioned within the intramural segment, the surface area of the first electrode 32 is made relatively significantly greater than the surface area of the second electrode 34. Preferably, the surface area of the first electrode 32 is at least about three to about ten times greater than the surface area of the second electrode 34. In this way, the first electrode 32 acts as a heat sink, absorbing any heat which is generated from the surrounding tissue. The significantly smaller surface area of the second electrode 34 prevents it from drawing any heat away from the surrounding tissue and, accordingly, heating of the tissue and formation of a lesion occur in proximity to the second electrode 34 and within the intramural segment 30 of the fallopian tube. In addition, if some heating did occur within the tissue in contact with the first electrode 32, this would not cause harm to the patient since it would be inside the uterus.

It should be understood that the tubal sterilization device having sesquipolar electrodes of the present invention is not intended to char or burn the walls of the fallopian tube 20. Rather, it is the healing process which ultimately occludes the treated fallopian tube. The initial response of the healing of the fallopian tube is an inflammatory response that then begins to close the tube. Over time, the tissue fibroses, and the lumen closes or is obliterated. It may require from two to four weeks before complete tubal occlusion occurs.

The tubal sterilization device of the present invention is flexible and easily maneuverable by a physician, and its proper positioning may be directly visualized using a hysteroscope. Furthermore, the device is inserted transcervically and obviates the need for surgery to effect sterilization. Because all RF energy travels between the two electrodes, stray currents and unintended heating is minimized.

The particular conical shape of the electrode tip 36 will help open the tubal osteum 28 without needing to insufflate the uterus with carbon dioxide gas or a saline solution. Furthermore, the shape of the conical surface of the electrode tip 36 will help to blindly place the device into the tubal osteum 28. Additionally, the active electrode 34 may be retracted into the conical structure of the electrode tip 36 to make the catheter 2 easier to insert and position, without perforating sensitive tissue or the thin wall of the fallopian tube 20. The particular shape of the electrode tip 36, with its conical first portion 38 and axially extendable second portion 40, allows proper positioning in the tubal osteum 28 and extension into the intramural segment 30 of the fallopian tube so that application of RF energy will be safer and reduce any risk of heating adjacent structures such as the bladder or bowel.

Heating is controlled by the feedback loop to prevent unnecessary burning or scorching of the targeted tissue. Furthermore, no foreign body is left behind in the patient to cause a reaction or affect future imaging with use of the tubal sterilization device of the present invention.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A tubal sterilization device, which comprises:

a hollow catheter defining an interior passageway, the catheter including a first end for insertion transcervically into a patient, and a second end opposite the first end for grasping and manipulation by a physician, at least a portion of the catheter being generally circular in cross-section and being sized for transcervical insertion into a fallopian tube of a patient;

an electrode tip situated at the first end of the catheter, the electrode tip including a first portion being blunt so as not to perforate patient tissue and having a first electrode situated thereon, and a second portion having a second electrode situated thereon, the second portion of the electrode tip being selectively spaced from the first portion of the electrode tip and movable axially relative thereto, the electrode tip being responsive to RF (radio frequency) energy to cause heating of at least a portion of the fallopian tube contacting the electrode tip when the electrode tip is received thereby, the first portion of the electrode tip including a bore formed axially therethrough, the second portion of the electrode tip being selectively received by the bore of the first portion, the second portion of the electrode tip including an insulating support, the second electrode being situated on the insulating support, the second electrode being formed as a coiled wire helically wrapped about and supported by at least a portion of the insulating support, the insulating support and coiled wire being selectively receivable by the bore of the first portion of the electrode tip; and a slider linkage extending through the catheter passageway and coupled to the second portion of the tip electrode, the slider linkage being axially movable within the catheter passageway, whereby axial movement of the slider linkage causes corresponding axial movement of the second portion of the electrode tip with respect to the first portion of the electrode tip, the insulating support being operatively coupled to the slider linkage, the second portion of the electrode tip, the insulating support and the coiled wire supported thereby being selectively received by the bore of the first portion in response to axial movement of the slider linkage within the catheter passageway.

2. A tubal sterilization device as defined by claim 1, wherein each of the first electrode and the second electrode includes an exposed surface area for contacting tissue of the fallopian tube of a patient, the surface area of the first electrode being greater than the surface area of the second electrode.

3. A tubal sterilization device as defined by claim 2, wherein the exposed surface area of the first electrode is at least about three to about ten times greater than the exposed surface area of the second electrode.

4. A tubal sterilization device as defined by claim 2, wherein the first portion of the electrode tip is generally conically-shaped, and wherein the second portion of the electrode tip is elongated axially in shape.

5. A tubal sterilization device as defined by claim 1, wherein the insulating support includes at least one electrical conductor situated interiorly thereof, the at least one electrical conductor being electrically connected to the second electrode.

6. A tubal sterilization device as defined by claim 1, which further comprises: an RF signal generator, the RF signal generator generating RF energy and providing the RF energy to the first and second electrodes.

7. A tubal sterilization device as defined by claim 6, which further comprises:

a power control circuit; and a temperature sensor, the temperature sensor being mounted on the electrode tip, the temperature sensor sensing the temperature of the portion of the fallopian tube being heated and providing a signal indicative thereof, the power control circuit being responsive to the signal from the temperature sensor and, in response thereto, generating a control signal, the RF signal generator being responsive to the control signal of the power control circuit and adjusting the power of the RF energy provided to the at least first and second electrodes in response thereto.

8. A tubal sterilization device as defined by claim 7, wherein the temperature sensor is situated on the second portion of the electrode tip.

* * * * *